United States Patent [19]

Denny et al.

[11] 4,065,464
[45] Dec. 27, 1977

[54] PROCESS FOR THE PREPARATION OF SUBSTITUTED TRICHLOROACETAMIDINE DERIVATIVES

[75] Inventors: George H. Denny; Walfred S. Saari, both of Lansdale, Pa.

[73] Assignee: Merck & Co., Inc., Rahway, N.J.

[21] Appl. No.: 691,279

[22] Filed: June 1, 1976

[51] Int. Cl.$^2$ .......................................... C07D 209/14
[52] U.S. Cl. ................................. 260/326.15; 560/251
[58] Field of Search .................................... 260/326.15

[56] References Cited

U.S. PATENT DOCUMENTS 2,855,398  10/1958   Voegtli ........................... 260/326.15

OTHER PUBLICATIONS

Gautier et al., The Chemistry of Amidines and Imidates, 1975, John Wiley & Sons, pp. 310–311.

Primary Examiner—Ethel G. Love
Attorney, Agent, or Firm—David L. Rose; J. Jerome Behan

[57] ABSTRACT

Substituted trichloroacetamidine derivatives are prepared by reacting trichloroacetamidine with an appropriately substituted compound also substituted with a suitable leaving group. The leaving groups are halogen, quaternary or tertiary amines, methanesulfonate, toluenesulfonate, and the like.

5 Claims, No Drawings

PROCESS FOR THE PREPARATION OF SUBSTITUTED TRICHLOROACETAMIDINE DERIVATIVES

SUMMARY OF THE INVENTION

This invention is related to a novel process for the preparation of certain trichloroacetamidine derivatives. Specifically this process is concerned with the reaction of trichloroacetamidine with an appropriately substituted substrate containing a leaving group. Thus it is an object of this invention to describe the process for the reaction of trichloroacetamidine with such substrate. A further object of this invention is to describe the suitable leaving groups. Further objects will become apparent from a reading of the following description of the invention.

DESCRIPTION OF THE INVENTION

N-(3-indolylmethyl) trichloroacetamidine and N-(2-acetoxy-3-phenoxypropyl) trichloroacetamidine are potent cardiotonic agents. A cardiotonic agent stimulates the contractile force of the heart muscle and thus increases the cardiac output. A cardiotonic agent is required for the treatment of congestive heart failure which results when the heart pumps less blood than is required by the metabolic demands of the body. The objective of treatment of congestive heart failure is to restore the balance of supply and demand for blood. This can be achieved through the instant cardiotonic agents which improve myocardial contractility and influence cardiac output to meet the demands of the body.

The above compound are prepared by reacting trichloroacetamidine with the appropriately substituted substrate containing a leaving group as seen in the following reaction scheme:

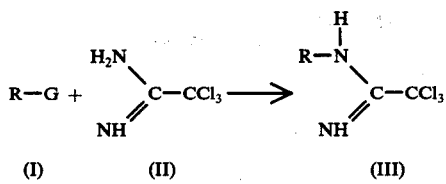

wherein R is 3-indolylmethyl or 2-acetoxy-3-phenoxypropyl; and G is a leaving group.

In the foregoing reaction the nature of the leaving group G is not critical so long as it is capable of being removed from the substrate (I) under the influence of trichloroacetamidine (II). Of course, one skilled in this art will realize that not all leaving groups will be removed from the substrate at the same rate; some will be faster or slower than others. However, the speed of this reaction is not critical so long as the leaving group can be removed from the substrate under the conditions employed without having any influence on the remainder of the molecule.

Leaving groups which are suitable for this reaction are halogens, tertiary amines, quaternary amine, sulfonic acid derivatives such as loweralkyl sulfonate, preferably methanesulfonate, aromatic sulfonates, preferably toluenesulfonate and the like.

The reaction is carried out by contacting trichloroacetamidine (II) with the substrate (I) preferably in a solvent, and heating the reaction mixture, preferably at the reflux temperature of the reaction mixture, for from 5 minutes to 6 hours. The choice of the solvent is not critical, however polar solvents are preferred when the substrate is a tertiary amine since such molecules are generally more soluble in polar solvents. For the other substrates, polar or non-polar solvents may be employed with equal facility. Loweralkanols, hydrocarbons, halogenated hydrocarbons, ketones, ethers, dimethylformamide, dimethylsulfoxide, hexamethylphosphoramide, tetrahydrofuran, and the like are acceptable.

Occasionally the initial combination of the substrate and the trichloroacetamidine may produce an exothermic reaction. In such cases the reagents are initially combined at room temperature, or lower if necessary, and the trichloroacetamidine or solution thereof, added dropwise to the substrate. The addition may take from 1 to 15 minutes, and when it is completed, the reaction is heated as previously described.

The product is isolated from the reaction mixture by procedures known to those skilled in the art.

The substrates (I) are generally described in the literature or procedures capable of producing them are known to those skilled in the art. The quaternary amines are generally obtained initially as a tertiary amine and converted to the quaternary amine by treatment with an alkyl halide such as methyl iodide. Appropriate tertiary amine starting materials for the instant process may be derived from 3-aminomethyl indole and 2-acetoxy-3-phenoxy propylamine in which the amine group of each molecule is additionally substituted by two other groups. The groups may be any organic moieties, however one will readily recognize that the more simple types of groups (alkyl, aromatic hydrocarbon, pyridine and the like) will be easier to prepare. In the case of pyridine substituted tertiary amines, the pyridine moiety will encompass the tertiary amine atom. Thus the tertiary amine is treated with an alkyl halide such as a loweralkyl iodide, preferably methyl iodide, generally at room temperature in a reaction which is complete in less than 1 hour. The quaternary amine is isolated using well known techniques, and reacted with the trichloroacetamidine as above described.

In the case of the 2-acetoxy-3-phenoxypropyl group, it is sometimes advantageous to utilize the corresponding 2-hydroxy compound as the starting material and to acylate the product recovered from the reaction with the trichloroacetamidine. The acylation is carried out utilizing procedures known to those skilled in the art.

Since the product and some of the starting materials of this process are basic compounds, it is possible, and may be desirable to employ the acid addition salt of such starting materials, or to isolate the product in the form of the acid addition salt. The mineral acid salts such as hydrohalide (hydrochloride), nitrate, sulfate, and the like are preferred. They may be prepared from the free base, and the free base is liberated therefrom by procedures known to those skilled in the art.

The following examples are provided in order that the invention might be more fully understood. They are not to be construed as being limitative of the invention.

EXAMPLE 1

N-(3-Indolylmethyl) trichloroacetamidine

A solution of gramine methiodide (31.6 g., 0.1 mole) in 250 ml. of ethanol is treated dropwise over a period of 30 minutes with a solution of trichloroacetamidine (16.1 g., 0.1 mole) in 50 ml. of ethanol. The solution is refluxed for 15 minutes, cooled and the solvent removed in vacuo to give a crystalline residue. The residue is partitioned between 150 ml. portions of chloroform and water and the water layer back-extracted with chloroform. The combined chloroform extracts are washed with water, dried over magnesium sulfate, filtered and concentrated in vacuo affording N-(3-indolylmethyl)-trichloroacetamidine m.p. 135.5 to 138.5 after recrystallization from benzene/hexane.

EXAMPLE 2

N(3-Indolylmethyl) trichloroacetamidine

A solution of 8.3 g. (0.05 mole) of 3-(chloromethyl) indole in 30 ml. of ether is mixed with a solution of 8.1 g. (0.05 mole) of trichloroacetamidine, also in ether. The mixture is heated at reflux for 3 hours, and concentrated in vacuo to an oil. This is taken up in warm chloroform, filtered, and the chloroform extracts washed first with water and then with dilute hydrochloric acid. The aqueous layers are combined, made basic with a saturated aqueous solution of sodium bicarbonate and the product extracted with chloroform. The combined chloroform extracts are washed with water, dried over magnesium sulfate, filtered and concentrated in vacuo affording N-(3-indolylmethyl) trichloroacetamidine m.p. 135.5 to 138.5 after recrystallization from benzene/hexane.

EXAMPLE 3

N-(2-Acetoxy-3-phenoxypropyl) trichloroacetamidine hydrochloride

A solution of 9.3 g. (0.05 mole) of 1-chloro-2-hydroxy-3-phenoxypropane in 100 ml. of tetrahydrofuran is mixed with a solution of 8.1 g. (0.05 mole) of trichloroacetamidine, also in tetrahydrofuran. The mixture is heated at reflux for 3 hours, and concentrated to an oil, which is taken up in benzene and washed well with water. The benzene layer is dried over magnesium sulfate, filtered, and treated with excess ethanolic hydrogen chloride to provide the crude hydroxy amidine hydrochloride. This is dissolved in glacial acetic acid and converted to the acetate by treatment with 3.5 g. (0.04 mole) of acetyl chloride at room temperature for 3 days. The reaction mixture is evaporated, treated with benzene, evaporated to dryness, and the process repeated once more with benzene, twice with toluene and twice with petroleum ether. There is afforded N-(2-acetoxy-3-phenoxypropyl) trichloroacetamidine hydrochloride, m.p. 70° to 77° C.

What is claimed is:

1. A process for the preparation of a compound having the formula:

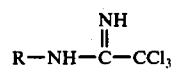

wherein R is 3-indolylmethyl, which comprises treating with trichloroacetamidine a compound having the formula:

R-G wherein R is as previously defined and G is a leaving group selected from a halide, an amine substituted with two groups selected from loweralkyl or aromatic hydrocarbon and loweralkyl quaternary derivatives thereof; pyridyl, loweralkylsulfonate and an aromatic sulfonate at reflux temperature for from 5 minutes to 6 hours.

2. The process of claim 1 in which the halide leaving group is chloro.

3. The process of claim 1 in which the sulfonic acid leaving group is a loweralkyl sulfonate or an aromatic sulfonate.

4. The process of claim 3 in which the loweralkyl sulfonate is methanesulfonate.

5. The process of claim 3 in which the aromatic sulfonate is toluenesulfonate.

* * * * *